(12) United States Patent
Pozzi

(10) Patent No.: US 11,235,914 B2
(45) Date of Patent: Feb. 1, 2022

(54) DEVICE FOR PACKAGING AND DISPENSING A PRODUCT, WITH VIAL AND DISPENSING MOUTHPIECE EQUIPPED WITH A FILTER

(71) Applicants: Horus Pharma, Saint-Laurent-du-Var (FR); Santen SA, Geneva (CH)

(72) Inventor: Jacques Pozzi, Antibes (FR)

(73) Assignees: Horus Pharma; Santen SA

( * ) Notice: Subject to any disclaimer, the term of this patent is extended or adjusted under 35 U.S.C. 154(b) by 0 days.

(21) Appl. No.: 17/053,226

(22) PCT Filed: May 7, 2019

(86) PCT No.: PCT/EP2019/061679
§ 371 (c)(1),
(2) Date: Nov. 5, 2020

(87) PCT Pub. No.: WO2019/215149
PCT Pub. Date: Nov. 14, 2019

(65) Prior Publication Data
US 2021/0070510 A1    Mar. 11, 2021

(30) Foreign Application Priority Data
May 7, 2018   (FR) ...................................... 1800464

(51) Int. Cl.
*B65D 47/18*      (2006.01)
*B65D 47/32*      (2006.01)
(Continued)

(52) U.S. Cl.
CPC ............. *B65D 47/18* (2013.01); *B65D 47/32* (2013.01); *A61F 9/0008* (2013.01); *B05B 11/007* (2013.01); *B65D 47/2031* (2013.01)

(58) Field of Classification Search
None
See application file for complete search history.

(56) References Cited

U.S. PATENT DOCUMENTS 2,772,817 A * 12/1956 Jauch ................... F04B 43/0063
222/207
4,513,891 A * 4/1985 Hain ..................... A61M 15/08
222/213
(Continued)

FOREIGN PATENT DOCUMENTS

EP    1773676 B1    5/2010
FR    2368306 A2    5/1978
(Continued)

OTHER PUBLICATIONS

French Search Report for Application No. FR1800464 dated Jan. 25, 2019, 2 pgs.
(Continued)

*Primary Examiner* — David P Angwin
*Assistant Examiner* — Michael J. Melaragno
(74) *Attorney, Agent, or Firm* — Lerner, David, Littenberg, Krumholz & Mentlik, LLP

(57) ABSTRACT

The device (100) for packaging and dispensing a product, liquid or in gel form, optionally for an ophthalmic application, comprises a container (1) containing the product to be dispensed by a dispensing head (7), as well as a refilling and filtering assembly for the air entering the container (1) after a dispensing, the dispensing head delimiting one or more dosing chambers (5) and including at its end a flexible part (7) which can be actuated to allow the release of the dose of product in a compressed state of said chamber (5). The air refilling and filtering assembly has a sterilizing filter (11) which cooperates with a check valve (12), this assembly (11, 12) being typically located in a central or inner portion of the head (7). The supply of outside air is accomplished by means of a channel (16) leading to an outer orifice (10) able to be obturated by a cover (15).

19 Claims, 3 Drawing Sheets

(51) Int. Cl.
*A61F 9/00* (2006.01)
*B05B 11/00* (2006.01)
*B65D 47/20* (2006.01)

(56) References Cited

U.S. PATENT DOCUMENTS

| | | | | |
|---|---|---|---|---|
| 4,646,945 A * | 3/1987 | Steiner | A47K 5/1209 | 222/207 |
| 4,776,495 A * | 10/1988 | Vignot | A47K 5/1209 | 222/206 |
| 4,991,745 A * | 2/1991 | Brown | B65D 35/12 | 137/493 |
| 5,082,150 A * | 1/1992 | Steiner | B67D 1/0079 | 222/189.09 |
| 5,238,153 A * | 8/1993 | Castillo | B05B 11/0072 | 222/189.09 |
| 5,259,956 A * | 11/1993 | Mercer | B01D 35/02 | 210/453 |
| 5,472,122 A * | 12/1995 | Appleby | B65D 47/2031 | 222/212 |
| 5,730,327 A * | 3/1998 | Stern | A47K 5/1209 | 222/105 |
| 6,073,812 A * | 6/2000 | Wade | A47K 5/1215 | 137/68.11 |
| 6,523,711 B1 * | 2/2003 | Hughes | A47G 19/2266 | 215/308 |
| 7,303,098 B2 * | 12/2007 | Backes | B65D 47/18 | 222/212 |
| 7,971,753 B2 * | 7/2011 | Mihashi | B65D 83/0055 | 222/95 |
| 7,971,755 B2 * | 7/2011 | Faurie | B65D 47/18 | 222/189.09 |
| 8,056,766 B2 * | 11/2011 | Grevin | B65D 47/18 | 222/189.06 |
| 8,616,418 B2 * | 12/2013 | Painchaud | B05B 11/00444 | 222/422 |
| 8,695,856 B2 * | 4/2014 | Nilsson | A47K 5/1209 | 222/207 |
| 8,701,942 B2 * | 4/2014 | Nilsson | A47K 5/1209 | 222/207 |
| 8,708,200 B2 * | 4/2014 | Nilsson | A47K 5/1209 | 222/207 |
| 8,752,732 B2 * | 6/2014 | Evans | A47K 5/1215 | 222/1 |
| 9,596,963 B2 * | 3/2017 | Harris | B05B 11/00442 | |
| 9,648,992 B2 * | 5/2017 | Harris | A47K 5/1211 | |
| 10,160,590 B2 * | 12/2018 | Wells | B65D 83/38 | |
| 2002/0153386 A1 * | 10/2002 | Uetake | B65D 47/2018 | 222/1 |
| 2004/0074925 A1 * | 4/2004 | Faurie | A61F 9/0008 | 222/212 |
| 2005/0139611 A1 * | 6/2005 | Kubo | B65D 47/18 | 222/189.06 |
| 2007/0032775 A1 * | 2/2007 | Niedospial, Jr. | A61J 1/2096 | 604/415 |
| 2007/0145076 A1 * | 6/2007 | Yamada | A61F 9/0008 | 222/189.09 |
| 2008/0296320 A1 * | 12/2008 | Kang | A45D 34/042 | 401/156 |
| 2008/0302828 A1 * | 12/2008 | Pozzi | B65D 47/2056 | 222/189.09 |
| 2009/0223883 A1 * | 9/2009 | Grevin | B65D 51/1616 | 210/151 |
| 2009/0318883 A1 * | 12/2009 | Sugahara | A61F 9/0008 | 604/298 |
| 2010/0044395 A1 * | 2/2010 | Webb | B65D 47/18 | 222/148 |
| 2010/0084397 A1 * | 4/2010 | Kubo | B65D 47/18 | 220/256.1 |
| 2010/0096416 A1 * | 4/2010 | Painchaud | B65D 51/18 | 222/496 |
| 2010/0108712 A1 * | 5/2010 | Manesis | A61F 9/0008 | 222/1 |
| 2011/0163114 A1 * | 7/2011 | Webb | A61J 1/1443 | 222/1 |
| 2011/0278323 A1 * | 11/2011 | Pozzi | B65D 47/18 | 222/108 |
| 2012/0310185 A1 * | 12/2012 | Defemme | B65D 47/18 | 604/296 |
| 2014/0124541 A1 * | 5/2014 | Mathiez | B65B 3/04 | 222/207 |
| 2014/0197207 A1 * | 7/2014 | Pozzi | B05B 11/00444 | 222/189.09 |
| 2015/0043958 A1 * | 2/2015 | Painchaud | B65D 47/2081 | 401/262 |
| 2016/0311588 A1 * | 10/2016 | Wochele | B65D 51/1616 | |
| 2017/0020726 A1 * | 1/2017 | Labombarbe | B65D 83/0094 | |
| 2017/0096266 A1 * | 4/2017 | Paganuzzi | A61F 9/0008 | |
| 2017/0224531 A1 * | 8/2017 | Chauhan | A61J 1/1456 | |
| 2018/0078456 A1 * | 3/2018 | Defemme | B01D 71/028 | |
| 2020/0055644 A1 * | 2/2020 | Hohm | B65D 47/2056 | |

FOREIGN PATENT DOCUMENTS

| | | |
|---|---|---|
| FR | 2873358 A1 | 1/2006 |
| FR | 2941682 A1 | 8/2010 |
| GB | 1563749 A | 3/1980 |

OTHER PUBLICATIONS

International Search Report for Application No. PCT/EP2019/01679 dated Jul. 5, 2019, 2 pgs.

* cited by examiner

FIG. 1
FIG. 2
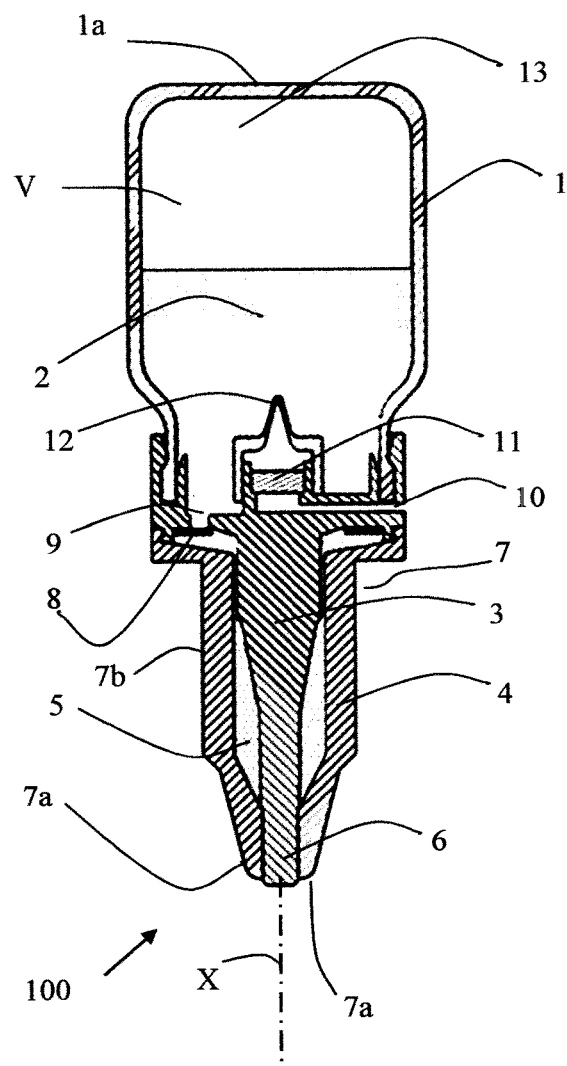
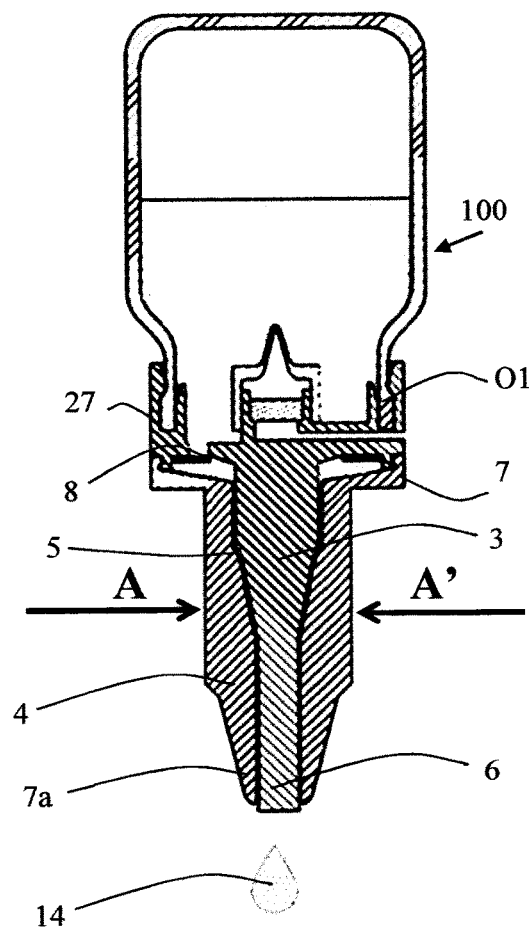

FIG. 3
FIG. 4
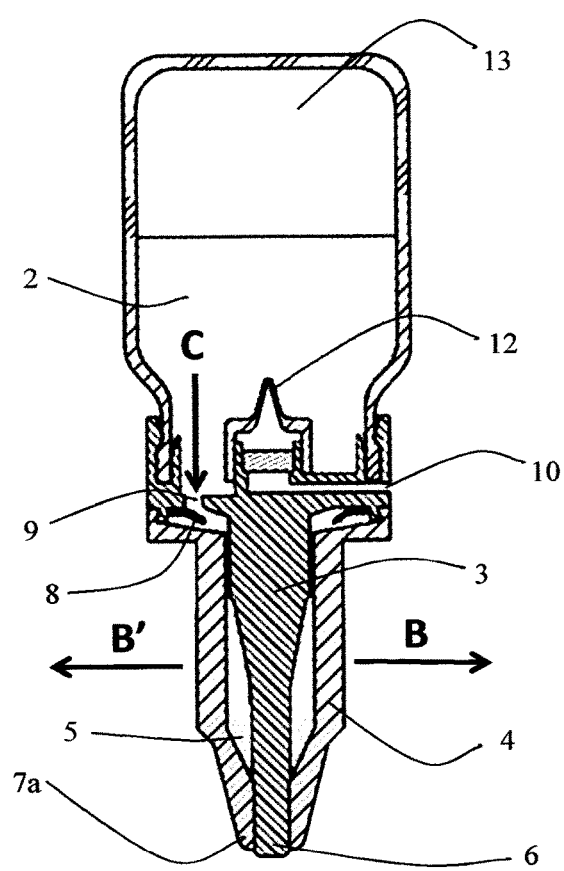
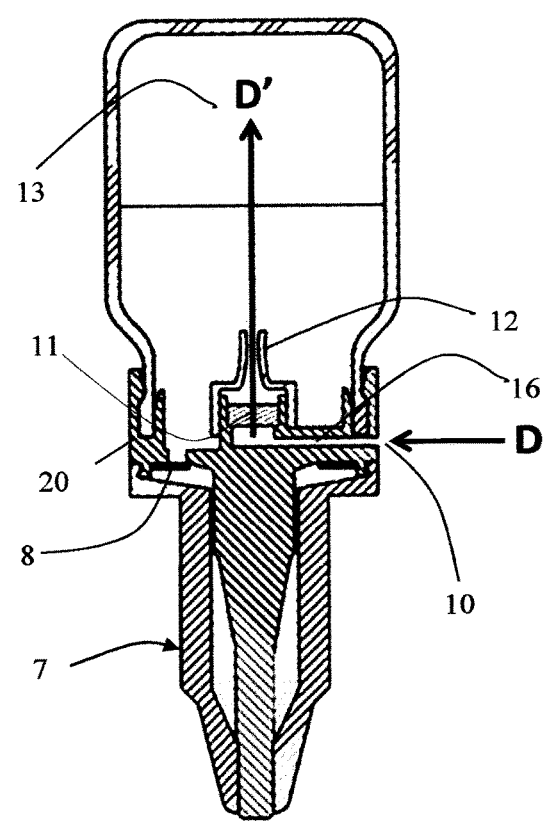
FIG. 5
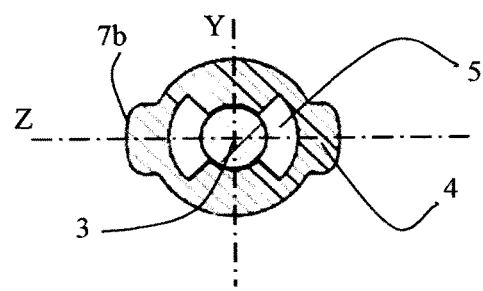

FIG. 6
FIG. 7
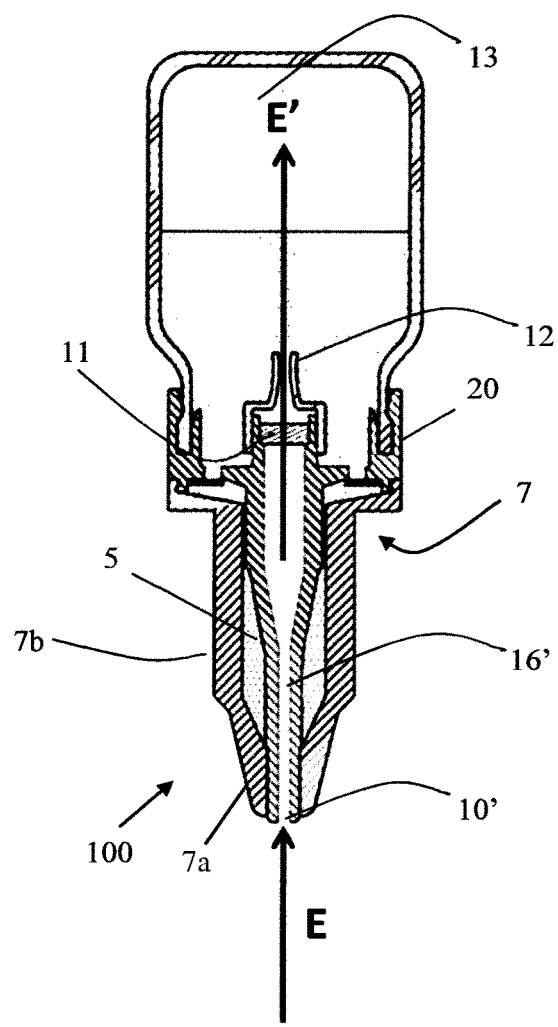
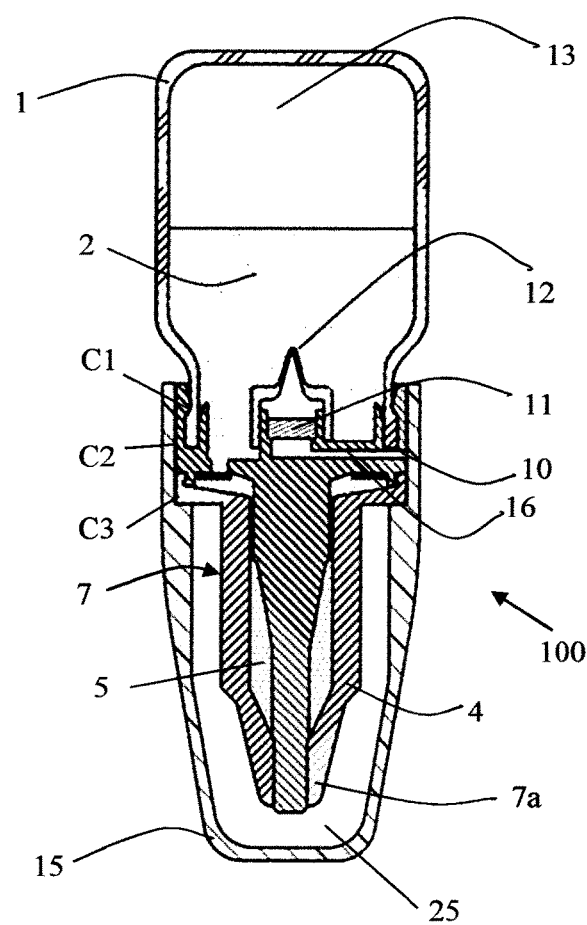

DEVICE FOR PACKAGING AND DISPENSING A PRODUCT, WITH VIAL AND DISPENSING MOUTHPIECE EQUIPPED WITH A FILTER

CROSS-REFERENCE TO RELATED APPLICATIONS

The present application is a national phase entry under 35 U.S.C § 371 of International Application No. PCT/EP2019/061679 filed May 7, 2019, which claims priority from French Application No. 1800464 filed May 7, 2018, all of which are hereby incorporated herein by reference.

TECHNICAL FIELD OF THE INVENTION

The present invention relates to the technical field of packaging fluid products, and more specially to that of packaging and dispensing a product that is liquid, semi-fluid or in suspension, intended to be preserved in a sealed and sterile manner, typically without the addition of preservative, and to be dispensed in the form of accurate unit doses by means of a dispensing assembly equipped with a mouthpiece.

More particularly, the invention relates to a device for packaging and dispensing of a sterile product, and which comprises:
a container intended to contain the product to be dispensed, and
a dosing assembly adapted to dispense a dose of the product, this assembly or dosing head comprising a dispensing end for dispensing the portion or dose of the product, and a mounting interface equipped with a fixation portion of the dosing assembly to the container.

TECHNICAL BACKGROUND OF THE INVENTION

Such devices are known, patent FR 2873358 (see also its equivalent, EP 1773676) describing for example a device of which the dispensing mouthpiece is of the type without an air intake. Dispensing is actuated by pressure exerted against a flexible wall of the container. The container, made of plastic, is obtained typically by injection molding. After dispensing, refilling with air results from pressure re-balancing allowed by means of an intake orifice (re-balancing to compensate for the depression created by the dispensing of the product). The air intake orifice is placed in the bottom of the container or in the mouthpiece, and is associated with a filter element. The filter element is used so as to sterilize the air entering the container.

The actuation of the dispensing is not necessarily very accurate with this type of device, the actuation zone being very distant from the dispensing end of the mouthpiece.

Patent FR 2873358 describes a valve associated with the filter and operating so that it can allow air to enter into the container while preventing any departure of air or liquid outside of the vial.

In devices having this kind of complex dispensing head, which can be actuated by pressure on the mouthpiece, the air intake assembly is formed at the bottom of the container.

However, the association of the filter element and of the vial implies that the bottom must be rigid and have accurate dimensions, which in practice limits its manufacture to injection molding using plastics.

With such type of device integrating the filter at the bottom of the vial, the de-molding operation necessitates that the container has a cylindrical shape and is equipped with an outlet neck with sufficiently large dimensions. This limits the marketing opportunities for the device.

In addition, this type of device is not simple to miniaturize.

The important dimensions of the outlet neck which must necessarily be at least equal to those of the inside of the body of the vial so that it can be de-molded impose large dispensing assembly dimensions so that it is adapted to the dimensions of the neck. The importance of these dimensions causes an increase in the manufacturing costs of the parts included in this dispenser.

Another disadvantage of existing devices resides in the fact that the filter is a source of fragility. The deterioration of the filter by an outside action (involuntary or not) makes the device inoperable.

Another disadvantage of existing devices resides in the fact that as the air refilling intake orifice is located in the bottom of the vial, the latter can be plugged or the filter clogged by simple contact with a liquid, making impossible the replacement of air.

Another disadvantage of existing device resides in the fact that the air refilling intake orifice being located in the bottom of the vial, the latter allows communication from the inside of the vial to the outside atmosphere, thus allowing pressure variations detrimental to the good operation of the device and able to cause liquid leaks to the outside of the bottle.

There exists therefore a need for reliable devices compatible with mass manufacturing methods, at least as regards the vial (i.e. a bottle preferably with a compact/small size), typically by allowing:
the use of vials made of plastic of any shape, not necessarily cylindrical, and/or
the use of vials manufactured from materials other than plastic, such as glass or aluminum for example, and/or
the manufacture of the neck of the vial with dimensions independent from the shape of the body of said vial.

Alternatively, or additionally, it would be desirable that the devices of the aforementioned type be equipped with a dispensing accessory adaptable to the neck of the vial with dimensions as small as possible and consequently much cheaper than that of existing devices.

It is a further aim of the invention to have a dispensing device with an assembly for refilling and filtering air protected against external elements, such as an inadvertent knock by the user or the same, while having a compact and simple design.

More generally, the invention aims at solving the drawbacks of devices of the state of the art and to propose such a dispensing device with is better suited to the various requirements of practice than known devices.

GENERAL DESCRIPTION OF THE INVENTION

The invention aims at improving the situation by mitigating one or more of the above-mentioned disadvantages.

To this end there is proposed a packaging and dispensing device for a product, generally a liquid or gel product (for example a generally semi-fluid liquid composition or a mixture with particles in suspension), the device comprising:
a container delimiting an internal volume and intended to contain the product,
a dispensing head, provided with a dispensing end and an actuating part, for dispensing a portion or dose of the product;

a mounting interface, belonging to the dispensing head and adapted to be fixed onto the container by a fixing portion, preferably annular;

an assembly for refilling and filtering air, the assembly for refilling and filtering air comprising an outer air intake orifice and a check valve (i.e. a non-return valve) allowing the air to enter through the outer opening in order to penetrate the internal volume after a product dispensing (i.e. the air passes through the outer opening to go inside the internal volume after one dispensation of the product);

characterized in that the outer orifice is formed at a distance from a bottom of the container, the assembly for refilling and filtering air comprising a filter element which is:

mounted in the dispensing head;

placed in an air circulation duct which extends between the outer orifice and the check valve; and preferably at a distance and offset inwardly from at least one of the container and said fixing portion, even more preferably at a distance and offset inwardly from both the container and said fixing portion.

As mentioned, the check valve acts as a non-return valve allowing the air to enter through the outer opening in order to penetrate the internal volume after a product dispensing, while preventing any fluid to circulate in the other direction, i.e. from the internal volume towards the outer opening.

According to a preferred option, the shape and the dimensions of the dispensing head do not depend on those of the neck of the container (or similar end of the container), the assembly for refilling and filtering air being positioned in the inner side of the accessory forming the dispensing head so that it is not accessible from the outside. As a consequence, any type of container could be used which is particularly advantageous. In particular the shape and dimensions of the vial to be used with the accessory could be various.

In addition, said assembly can be obturated by the positioning of a cover.

With this arrangement, the assembly for refilling and filtering air is advantageously isolated in the inside of the vial, by making it inaccessible to any outside action which could either deteriorate it or make it inoperative.

The arrangement of the filter element at a distance from the container and/or from the fixing portion means, of course, an arrangement at a non-zero distance (which means that there exists spacing which is visible to the naked eye if the device were cut open).

This also allows reducing bulk and improves the compactness of the assembly. The dispensing head can be axially longer than it is wide, in one option.

In one embodiment, the dispensing head is axially tapered (narrower) toward the dispensing end, opposite to the container. The device thus has a compact head.

Advantageously, the device is of the type that can be actuated by pressure on one side of the dispensing head and/or by any type of compression of at least one dosing chamber. Thus, the check valve allows air previously filtered by the filter element to pass into the container, only after a dispensing or dispensation of a portion or dose of the product by compression of the dosing chamber(s).

By the use of a simple cover it is also possible to isolate the inside of the vial or container from outer pressure variations. In fact, the cover can sealingly obturate access to the outer orifice (where the air circulation duct leads).

According to a preferred embodiment, the dispensing end extends along a longitudinal direction, and the filter element is mounted in the dispending head axially aligned with the dispensing end along said longitudinal direction. This improves the compactness and miniaturization of the device.

Preferably, the air circulation duct is tubular and the filter element has a circular cross-section with dimensions to be mounted within a circular inner section of the tubular air circulation duct, for example by press fit.

Optionally, the filter element can be a simple disc or cylinder, made for example of fibrous material.

In one option, the filter element comprises a hydrophobic material or is made of hydrophobic material.

According to one feature, the outer orifice is formed in the dispensing head, outside of the actuating part.

According to one feature, the container has an opening opposite the bottom, and a side wall extending about a longitudinal axis, the mounting interface being fixed onto the container on the side of its opening and extending annularly about the longitudinal axis. The fixing portion is preferably annular to define a preferably radial, sealed annular contact against the container.

According to one feature, the container is formed in one piece.

Optionally, the wall of the container is less compressible than the actuating part, and it is preferably rigid.

The container forms an outer face of the device, all or part of the outer face being adapted to allow the grasping of the device.

Optionally, the duct leads radially to the outside, and/or the air circulation duct comprises a section which extends radially between a portion of the duct, preferably bent, including the outer orifice and a bent area located upstream of the filter element in the inflow direction of the circulation of air.

More generally, a segment, typically narrow, can be provided, which extends from the outer orifice to a bent or bypass area, preferably located upstream of the filter element in the inflow direction of the circulation of air.

With this disposition, the filter is no longer opposite the outer outlet of the duct, which improves its protection.

The filtration direction can be an axial direction, optionally parallel to the general air injection direction in the internal volume in an open side of the check valve. This disposition allows considerable miniaturization.

Alternatively, filtration can occur at least in part in a radial direction, centripetal for example. A configuration with centripetal filtration can optimize the surface of the filtering medium on the upstream side, in particular when the filtering medium has an annular conformation. Such an option can be provided for when it is desired to guarantee a very high filtration quality.

According to one option, the outer orifice forms a lateral outlet of the air circulation duct through an outer wall of the dispensing head, so that an entry section of the air circulation duct extends radially toward the filter element.

A cover can preferably be provided to cover the dispensing head and the outer orifice.

Preferably, the cover defines an annular sealed contact against the mounting interface, complementary to an annular sealed contact of the fixing portion against the container, in a hermetic storage configuration (with the cover mounted and fixed on the mounting interface). At least one of these contacts, preferably both contacts, are accomplished in a continuous radial contact area.

According to another option, the air circulation duct comprises an entry section which extends axially between:

the outer orifice;

and duct widening area, located upstream of the filter element in the inflow direction of the circulation of air.

It can be provided for that the outer orifice forms an axial inlet of the air circulation duct through the dispensing end, the duct possibly being formed by a rigid tubular element formed in one piece.

In various embodiments of the device according to the invention, it is possible also have recourse to one and/or the other of the following arrangements being taken alone or in combination:
- the filter element is mounted in the dispensing head and arranged to be placed in the internal volume of the container, preferably beyond the fixing portion.
- the filter element is mounted on the side of an inner face of the dispensing head which extends opposite the axial dispensing end.
- the filter element is positioned internally in a recess of the check valve.
- the air circulation duct comprises a narrow section extending between the external orifice and a widening area formed by, or communicating with, the central cavity.
- the partition element includes an (optionally transverse) base and a longitudinal extension formed in one piece.
- the check valve comprises an elastically deformable piece which forms a valve extended by a female element, the female element being connected sealingly to a tubular male portion belonging to the dispensing head.
- the tubular male portion forms part of a partition element which separates said internal volume from a dosing chamber, the tubular male portion being integrally formed with a rigid inner rod of the dispensing head which extends to the dispensing end (thus a single part can form the duct).
- the check valve is a duckbill check valve.
- the device comprises a removable cover adapted to be fixed to the mounting interface so as to cover the dispensing head, and to close (preferably sealingly) the outer orifice.
- the check valve has a valve formed integrally with a tubular fixing portion, this tubular fixing portion surrounding and being connected by a radial annular contact against and outer face of a tubular connector formed by the partition element.
- the dispensing head has two dosing chambers preferably distributed symmetrically on either side of a medial plane XY (separating two halves of the container), this median plane XY comprising the central axis X of the container and an axis Y perpendicular to the axis X and perpendicular to an axis Z defining the thrust direction on the actuating part associated with each dosing chamber.
- the dispensing head comprises a dosing chamber and a partition element separating the dosing chamber from the internal volume, a central cavity being formed by the partition element (the latter having for example a cylindrical or annular conformation) to allow housing and/or attaching the filter element, the central cavity constituting all or part of an end of the air circulation duct.
- the dispensing head is adapted to dispense a portion or dose of the product in response to a pressure exerted on the actuating part.

The pressure is typically accomplished on a flexible portion of the dispensing head, the head having a rigid part which remains immobile with respect to the container and which (partly) delimits the dosing chamber; thus, the device allows dispensing portions or doses of the product by simple pressure on the flexible portion of the mouthpiece with which the accessory is equipped, and to compensate the depression thus created in the container by (preferably sterile) the air refill through the refilling and filtering assembly positioned in the inside of said accessory in such a manner that it can be isolated from the outside.

Advantageously, the accessory (forming the dispensing head) in which the air refilling and filtering assembly is positioned consists of two parts separately molded and sealingly assembled, of which one flexible one allows the dispensing of a dose of product by the compression of a dosing chamber and the opening of its end by spreading the corresponding other rigid part, and said other rigid part including at its center the air refilling and filtering assembly composed of a filter and of a valve allowing the isolation of the filter from the liquid, and of an refilling air intake channel located either axially or laterally.

According to one feature, the filter element is a sterilizing filtering medium.

Optionally, the filter element cooperates with a one-way passage valve, allowing the outer air to penetrate the internal volume of the container (by joining a free space in the container which is complementary to the product), but not allowing the liquid product to escape outside of the container, or to come into contact with the filter element.

The device according to the invention can be used for packaging drops of a product for ophthalmic use or for other applications requiring accurate doses of a product preserved in sterile fashion in the container to be delivered.

The container is preferably produced in one piece.

The container can be made of glass.

The mounting interface is optionally formed by an adaptation ring (allowing adaptation to a variety of containers without modifying the structure of the functional portions of the accessory).

Other features and advantages of the invention will be revealed by the description below, with reference to the appended drawings, which show, by way of non-limiting examples, embodiments and implementations of the object of the invention. In these drawings:

FIG. 1 is a schematic view in axial section of an exemplary device conforming to the invention when it is not under load, showing a container containing the product to be dispensed, an accessory (the dispensing head) composed of two portions, one rigid and the other flexible, the flexible portion comprising buttons to impart pressure on dosing chambers delimited by said two portions, a product dispensing assembly composed of the end of the flexible portion in cooperation with the end of the rigid part, said dispensing assembly allowing the product to be expelled toward the outside when the chambers are compressed, but not allowing air to enter the inside of the container when said chambers are no longer under load, an air refilling and filtering assembly comprising a filter and a check valve positioned in the rigid part of said accessory;

FIG. 2 is a schematic view in axial section of a device according to FIG. 1 when it is under load, showing the accessory when the chambers are compressed and a dose of the product is expelled by means of the dispensing assembly;

FIG. 3 is a schematic view in axial section of a device according to FIG. 1 during the phase of filling the chambers with the product contained in the container when the chambers are no longer under load.

FIG. 4 is a schematic view in axial section of a device according to FIG. 1, showing the refilling air inflow circuit through a lateral channel, the filter and the valve.

FIG. 5 is a schematic view in transverse section of a device according to FIG. 1, showing the chambers delimited by the rigid and flexible portions.

FIG. 6 is a schematic view in axial section of a device according to a variant embodiment, showing the refilling air inflow circuit through a central channel, the filter and the valve.

FIG. 7 is a schematic view in axial section of a device according to FIG. 1, on which is positioned a cover obturating the refilling air intake orifice.

As shown in FIG. 1, the packaging and dispensing device 100 comprises a container 1 containing the product to be dispensed 2, and a dispensing accessory or dispensing head 7 composed of a rigid part 3 cooperating with a flexible portion 4, the assembly of these portions 3, 4 delimiting the dosing chambers 5. In the non-limiting example illustrated in FIGS. 1 and 2, the dosing chamber(s) 6 can be located completely outside the internal volume V delimited by the container 1. A partition element including or forming the rigid part 3 can form a separation between the internal volume V and the dosing chambers 5. The lateral wall of the container 1 extends around a longitudinal axis X (forming typically a central axis of the device 100) which can pass through the axial end 7a where the dose or drop 14 is expelled.

The end 7a of the flexible portion 4 cooperates with the end 6 of the rigid part 3 so as to allow the product contained in the chambers 5 to be expelled from the inside of said chambers 5 when they are compressed, but not allowing outside air to penetrate into said chambers 5 when they are no longer compressed. The actuation of the dispensing is allowed by at least one actuating part 7b, formed for example laterally on the dispensing head 7. The actuating part 7b is movable by depression, in the manner of a push-button.

In the non-limiting example of FIG. 5, each chamber 5 extends between the rigid part 3 (internal side) and an internal face of the flexible part 4 radially spaced from the rigid part. While the dispensing head 7 does not have an air intake opening in the lateral area covering the dosing chamber(s) 5, the dispensing head 7 is however equipped with an external orifice 10, 10' allowing pressure re-balancing after the dispensing of a dose, as clearly visible in FIGS. 4 and 6. Such an orifice 10, 10' is located on the side of an end of the dispensing head 7, or in the mounting interface 27, or surrounded by the end 7a opposite the mounting interface 27, in the axial extension of the dosing chambers 5.

The device 100 also comprises a check valve 8 allowing the product 2 to be sent from the inside of the container 1 toward the chamber(s) 5, but not allowing said product to return from the chambers 5 toward the inside of the container 1, an air refilling and filtering assembly comprising a sterilizing filter or similar filter element 11 associated with a valve 12 of the check-valve type (i.e. a non-return valve) which allows outside air to penetrate into the inside of the container 1 while preventing any departure of air or product 2 from the interior toward the outside of the container 1.

The content of the internal volume V thus remains sterile when the filter element 11 is of the sterilizing grade or has a sufficient barrier/screen effect. This type of filter element 11 is for example composed of polymers having pores of sub-micron size, for example on the order of 0.20 or 0.22 µm. To avoid any risk of clogging, the filter element 11 or a supply area upstream of this filter element can include a pre-filter.

It is understood that the outer orifice 10, 10' can be formed at a distance from the bottom 1a of the container 1, just like the air refilling and filtering assembly (11, 12) which includes the filter element 11. In a preferred embodiment, the filter element 11 is mounted in the dispensing head 7 by being placed in an air circulation duct 16 or 16' which extends between the outer orifice 10 or 10' and the check valve 12. The filter element 11 is for example inserted into a central cavity formed by the partition element which covers the internal volume V. The cavity forms here a widening area of the duct 16. The valve 12 can close this central cavity. Possibly, the valve 12 surrounds all or part of the filter element 11, for example so that the filter element 11 is placed interiorly in a recess of the check valve 12.

The filter element 11 extends at a distance and can be offset inwardly from at least one of the container 1 and the fixing portion 20 allowing snap-in sealing installation of the container 1 or a similar sealed fixing portion between the dispensing head 7 and the container 1.

Preferably, the filter element 11 extends at a distance and is offset inwardly from both the container 1 and the fixing portion 20. For instance, it can be arranged substantially centrally relative to the opening of the container, preferably axially aligned with the longitudinal shape of the dispensing end of the dispensing head.

The valve 8 can be fixed to the mounting interface 27, so that it is completely distant from the container 1, and preferably located outside the internal volume V. It can be seen in the drawings that this valve 8 (distant from the longitudinal axis X) can be closer to the annular fixation portion engaged with the container 1 than is the filter element 11, the latter being closer to the longitudinal axis X.

The device 100 as shown in FIGS. 2, 3, 4 and 5 operates in the following manner.

According to FIG. 2, a pressure exerted on the flexible part 4 (typically by targeting the actuating part(s) 7b) according to arrows A and A', compresses the product contained in the chambers 5 and expels said product toward the outside of the device 100 by means of the end 7a of the flexible part 4 which spreads away from the end 6 of the rigid part 3, then returns to its initial position under the influence of its own elasticity after having released a drop 14 of product.

Optionally, the dispensing head 7 has two dosing chambers 5 as in the example of FIGS. 1 and 5. These two chambers 5 are preferably distributed symmetrically on either side of a median plane XY (separating two halves of the container), this median plane XY comprising the central axis X of the container 1 and an axis Y perpendicular to the axis X and perpendicular to an axis Z defining the direction of thrust on the actuating part 7b associated with each dosing chamber 5.

According to FIG. 3, the flexible part 4 returns to its initial position according to arrows B and B' when the outside pressure ceases, creating a depression in the inside of the chambers 5 which causes the opening of the valve 8 and the passage of liquid 2 from the inside of the container 1 toward the inside of the chambers 5 through the orifice 9 according to arrow C (with a flow substantially parallel to the axis X, running along the central rod belonging to a rigid part 3 of the dispensing head 7).

The passage of a portion of the product 2 toward the inside of the chambers 5 has the effect of creating a depression in the free portion 13.

FIG. 4 shows the travel of the refilling of air so as to compensate this depression. The outside air penetrates into the container 1 through the orifice 10 of the lateral channel defining the duct 16 according to arrow D, then through the filter element 11 according to arrow D' and the elastic check valve 12 which opens under the effect of relative overpressure of the refilling air. When the depression existing in the free portion is compensated by the intake of the refilling air, this air intake ceases and the elastic valve 12 resumes its initial closed position, preventing any departure of said product 2 from the inside toward the outside of the device 100.

FIG. 6 shows the travel of the refilling air represented by arrows E and E' according to the same principle and that previously described, but through the orifice 10' of an axial channel forming the air circulation duct 16'.

FIG. 7 shows the device 100 at rest after the installation of a protection cover 15. Said cover 15 obturate the end (orifice 10) of the channel or duct 16 by cooperating sealingly with the accessory 7, by preventing any communication between the inside of the device 100 and the outside.

With reference to FIG. 7, it can be seen that the cover 15 defines an annular sealed contact C2 against the mounting interface 27, complementary to an annular sealed contact C1 of the fixing portion 20 against the container 1, in a hermetic storage configuration (with the cover 15 mounted and fixed to the mounting interface 27). At least one of these contacts, preferably both contacts C1, C2, are accomplished in a continuous area of radial contact.

The cover 15 can accomplish a sealed contact C3 against an external shoulder of similar external surface of the dispensing head 7, so as to prevent the air 25 imprisoned under the cover 15 15 from communicating with the air intake orifice 10, in a peripheral area around the mounting interface 27 where the duct 16 has its outlet (via the orifice 10).

The illustrated device 100 includes an air refilling and filtering assembly comprising a filter element 11 located at a location inaccessible from the outside, thus guaranteeing its complete integrity.

The shape and the dimensions of the dispensing head 7 or similar accessory completing the container 1 does not depend on those of the open end (typically the neck) of the container 1. The coupling of the air refilling and filtering assembly (11, 12) with the dispensing head 7 is compatible with a reduction of the size of this head 7 (smaller bulk) and allows hiding/protecting the filter element 11, which makes the device 100 more reliable (by minimizing the risk of degradation).

Other embodiments are possible without departing from the scope of the invention. For instance, it is possible to produce such a device 100 including only a single dosing chamber 5, or one or more dosing chambers with a different form from those shown in FIG. 5, such as for example a dosing chamber as described in patent EP 1773676.

Likewise, a dosing chamber delimited in the accessory forming the dispensing head 7 can extend at least in part to the inside of the internal volume V of the container 1, in variant embodiments.

The invention claimed is:

1. A device for packaging and dispensing a product, generally a liquid or gel product, comprising:
   a container delimiting an internal volume and intended to contain the product,
   a dispensing head, provided with a dispensing end and an actuating part, to dispense a portion or dose of the product;
   a mounting interface belonging to the dispensing head and adapted to be fixed onto the container by a fixing portion;
   an assembly for refilling and filtering air, said assembly comprising an outer air intake orifice and a check valve allowing air entering through the outer orifice to penetrate the internal volume after a product dispensing;
   wherein the outer orifice is formed at a distance from a bottom of the container, the assembly for refilling and filtering air comprising a filter element which is:
   mounted in the dispensing head;
   placed in an air circulation duct which extends between the outer orifice and the check valve; and
   at a distance and offset inwardly from both of the container and said fixing portion,
   wherein the dispensing end extends along a longitudinal direction, the filter element being mounted in the dispending head axially aligned with the dispensing end along said longitudinal direction.

2. The device according to claim 1, wherein the air circulation duct is tubular and the filter element has a circular cross-section with dimensions to be mounted within a circular inner section of the tubular air circulation duct.

3. The device according to claim 1, wherein the dispensing head comprises a dosing chamber and a partition element separating the dosing chamber from the internal volume, the partition element being preferably in the form of a rigid part, a central cavity being formed by the partition element to allow housing and/or attaching the filter element, the central cavity constituting all or part of an end of said air circulation duct.

4. The device according to claim 1, wherein the container has an opening opposite the bottom, and a side wall extending about a longitudinal axis, the mounting interface being fixed onto the container on the side of its opening and extending annularly about the longitudinal axis, said fixing portion being annular to define a preferably radial, sealed annular contact against the container.

5. The device according to claim 1, wherein the filter element is mounted in the dispensing head and arranged to be placed in the internal volume of the container, preferably beyond the fixing portion.

6. The device according to claim 1, wherein the filter element is mounted on the side of an inner face of the dispensing head which extends opposite the dispensing end.

7. The device according to claim 1, wherein the filter element is mounted internally in a recess of the check valve.

8. The device according to claim 1, wherein the check valve comprises an elastically deformable piece which forms a flap extended by a female element, the female element being sealingly connected to a tubular male portion belonging to the dispensing head.

9. The device according to claim 8, wherein the tubular male portion is part of a partition element which separates said internal volume from a dosing chamber, the tubular male portion being integrally formed with a rigid inner rod of the dispensing head which extends to the dispensing end.

10. The device according to claim 1, further comprising a removable cover adapted to cover both the dispensing head and the outer orifice.

11. The device according to claim 1, comprising a removable cover adapted to be fixed to the mounting interface so as to cover the dispensing head and close the outer orifice.

12. A device for packaging and dispensing a product, generally a liquid or gel product, comprising:
- a container delimiting an internal volume and intended to contain the product,
- a dispensing head, provided with a dispensing end and an actuating part, to dispense a portion or dose of the product;
- a mounting interface belonging to the dispensing head and adapted to be fixed onto the container by a fixing portion;
- an assembly for refilling and filtering air, said assembly comprising an outer air intake orifice and a check valve allowing air entering through the outer orifice to penetrate the internal volume after a product dispensing;
- wherein the outer orifice is formed at a distance from a bottom of the container, the assembly for refilling and filtering air comprising a filter element which is:
- mounted in the dispensing head;
- placed in an air circulation duct which extends between the outer orifice and the check valve; and
- at a distance and offset inwardly from both of the container and said fixing portion,
- wherein the outer orifice forms a lateral outlet of the air circulation duct through an outer wall of the dispensing head, so that an entry section of the air circulation duct extends radially toward the filter element.

13. The device according to claim 12, wherein the air circulation duct is tubular and the filter element has a circular cross-section with dimensions to be mounted within a circular inner section of the tubular air circulation duct.

14. The device according to claim 12, wherein the dispensing head comprises a dosing chamber and a partition element separating the dosing chamber from the internal volume, the partition element being preferably in the form of a rigid part, a central cavity being formed by the partition element to allow housing and/or attaching the filter element, the central cavity constituting all or part of an end of said air circulation duct.

15. The device according to claim 12, wherein the container has an opening opposite the bottom, and a side wall extending about a longitudinal axis, the mounting interface being fixed onto the container on the side of its opening and extending annularly about the longitudinal axis, said fixing portion being annular to define a preferably radial, sealed annular contact against the container.

16. A device for packaging and dispensing a product, generally a liquid or gel product, comprising:
- a container delimiting an internal volume and intended to contain the product,
- a dispensing head, provided with a dispensing end and an actuating part, to dispense a portion or dose of the product;
- a mounting interface belonging to the dispensing head and adapted to be fixed onto the container by a fixing portion;
- an assembly for refilling and filtering air, said assembly comprising an outer air intake orifice and a check valve allowing air entering through the outer orifice to penetrate the internal volume after a product dispensing;
- wherein the outer orifice is formed at a distance from a bottom of the container, the assembly for refilling and filtering air comprising a filter element which is:
- mounted in the dispensing head;
- placed in an air circulation duct which extends between the outer orifice and the check valve; and
- at a distance and offset inwardly from both of the container and said fixing portion,
- wherein the air circulation duct comprises an entry section which extends axially between:
- the outer orifice;
- and a duct widening area located upstream of the filter element in the inflow direction of the circulation of air, and
- wherein the outer orifice forms an axial inlet of the air circulation duct through the dispensing end, the duct being formed by a rigid tubular element formed in one piece.

17. The device according to claim 16, wherein the air circulation duct is tubular and the filter element has a circular cross-section with dimensions to be mounted within a circular inner section of the tubular air circulation duct.

18. The device according to claim 16, wherein the dispensing head comprises a dosing chamber and a partition element separating the dosing chamber from the internal volume, the partition element being preferably in the form of a rigid part, a central cavity being formed by the partition element to allow housing and/or attaching the filter element, the central cavity constituting all or part of an end of said air circulation duct.

19. The device according to claim 16, wherein the container has an opening opposite the bottom, and a side wall extending about a longitudinal axis, the mounting interface being fixed onto the container on the side of its opening and extending annularly about the longitudinal axis, said fixing portion being annular to define a preferably radial, sealed annular contact against the container.

* * * * *